United States Patent [19]

Swierczek

[11] Patent Number: 5,201,324
[45] Date of Patent: Apr. 13, 1993

[54] DISPOSABLE SKIN PERFORATOR AND BLOOD TESTING DEVICE

[76] Inventor: Remi Swierczek, 6399 Ledge Lake Ct., Concord, Ohio 44077

[21] Appl. No.: 732,109

[22] Filed: Jul. 18, 1991

Related U.S. Application Data

[63] Continuation-in-part of Ser. No. 566,160, Aug. 10, 1990, Pat. No. 5,054,499, which is a continuation-in-part of Ser. No. 328,907, Mar. 27, 1989, abandoned.

[51] Int. Cl.[5] ............................................... A61B 5/00
[52] U.S. Cl. ...................................... 128/770; 606/182
[58] Field of Search ................ 128/770; 606/181, 182, 606/185

[56] References Cited

U.S. PATENT DOCUMENTS

| | | | |
|---|---|---|---|
| 4,635,633 | 1/1987 | Hufnagle | 606/181 |
| 4,715,374 | 12/1987 | Maggio | 606/182 |
| 4,790,979 | 12/1988 | Terminiello et al. | 422/56 |
| 4,869,249 | 9/1989 | Crossman et al. | 606/182 |
| 4,892,097 | 1/1990 | Ranalletta et al. | 606/182 |
| 5,014,718 | 5/1991 | Mitchen | 128/771 |
| 5,026,388 | 6/1991 | Ingalz | 606/182 |
| 5,054,499 | 10/1991 | Swierczek | 128/770 |

FOREIGN PATENT DOCUMENTS 3515420 10/1986 Fed. Rep. of Germany ...... 128/770

Primary Examiner—Max Hindenburg
Assistant Examiner—Guy V. Tucker
Attorney, Agent, or Firm—Oldham, Oldham & Wilson Co.

[57] ABSTRACT

A device that pierces the skin due to the collapsing of dome between the fingertips. Immediately after a puncture is made, a blood or exudate sample can be collected on an absorbent test strip laminated on the pressure plate. Flow enhancement of blood or exudate from the puncture site is achieved by maintenance of pressure around the site and on the imparting of a vacuum within the device. A shutter device incorporated into the skin perforator prevents repeated use of the device.

22 Claims, 4 Drawing Sheets

DISPOSABLE SKIN PERFORATOR AND BLOOD TESTING DEVICE

This is a continuation-in-part of application Ser. No. 07/566,160, filed Aug. 10, 1990, which has been allowed as U.S. Pat. No. 5,054,499 and which was a continuation-in-part of application Ser. No. 07/328,907, filed Mar. 27, 1989, now abandoned.

TECHNICAL FIELD

This invention, generally, relates to a device for drawing a small amount of blood from a person's fingertip. More specifically, the invention relates to a device for obtaining a minute volume of blood and applying the same to a test medium for subsequent analysis. Another embodiment of the present invention relates to a single use device for obtaining a blood sample employing a means for preventing multiple use of the device.

BACKGROUND OF THE INVENTION

Blood testing is a common practice. The samples can be derived by merely pricking the fingertip with a sharp tool. Then, the samples must be exposed to proper test medium to acquire the test result.

In the past, a complex, sudden release, pen type device with disposable blades was used to perforate the skin painlessly. Once the skin was cut, separate test medium was introduced to the blood sample.

SUMMARY OF THE INVENTION

In accordance with the embodiments of the present invention, this device is a disposable skin perforator for obtaining a sample of blood by puncturing the skin. A further embodiment discloses a test medium attached to a pressure plate on the device which can absorb blood flowing from the puncture.

Therefore, one objective of my invention is to provide a simple, painless and inexpensive fingertip perforator that draws a sample of blood for testing and self-analysis.

Another objective of my invention is to provide a convenient holding means for litmus paper and other type test medium in such a way to allow for saturation of the test medium with blood while it is drawn.

A third objective of my invention is to provide a package that consists of a chart and bandage. The chart can be color coded to read the test results while the bandage can be used to protect the cut finger.

A further object of my invention is to provide a skin perforator for obtaining a blood sample which possesses a self-contained means for cleansing and/or disinfecting the puncture site, prior to perforation of the skin.

Still a further object of my invention is to provide a skin perforator for obtaining a blood sample which employs a means for preventing multiple use of the same device. Other objectives of my invention will become clear with reference to the accompanying figures.

DETAILED DESCRIPTION OF THE PREFERRED EMBODIMENT

Figure 1:
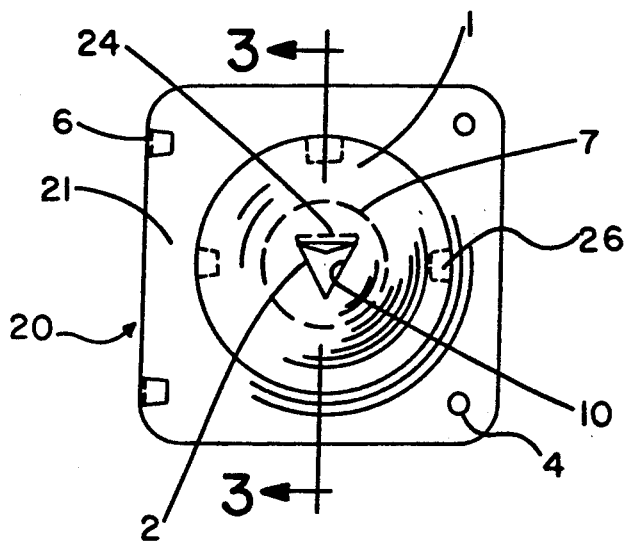
FIG. 1 is a plan view of the perforator device.

Now with reference to the invention illustrated in the drawings, and looking particularly at FIG. 1, this figure shows a top plan view of the perforator device 20. Perforator device 20 comprises generally a cover plate 21 and a pressure plate 3 of essentially similar size and shape positioned adjacent to one another and attached by a plurality of welds 4 and/or crimps 6.

Cover plate 21 has a spherical shaped dome 1 formed therein so as to define a convex surface with respect to said cover plate 21 and directed outward and away from said pressure plate 3. Cover plate 21 with spherical dome 1 formed integrally therein is made of a resilient plastic or thin metal material having a substantial memory so that as dome 1 is deflected inward by a force it will return to essentially its original shape upon the removal of said force.

Pressure plate 3 is to have a rigid structure as compared to dome 1 and may be made from any plastic or metal material capable of maintaining such rigidity. Welds 4 or crimps 6 of varying number and size are contemplated. Pressure plate 3 has an aperture 7 formed generally in the center of said pressure plate 3 and having sufficient diameter to allow the passage of a barb 2 through the aperture 7. Shelf 23 defines the periphery of said aperture 7.

A barb 2 is formed in a portion of dome 1 utilizing stamping methods which are well known in the art. Barb 2 remains integral with dome 1 along edge 24 of barb 2. Barb 2 is disclosed as being essentially triangular in shape however, any shape which yields a point capable of piercing the human skin is contemplated. The stamping of dome 1 to form barb 2 results in an aperture having essentially the same dimensions as said barb 2. Barb 2 is formed so as to be directed inward and toward the aperture 7 of plate 3. After stamping, barb 2 can be coined or shaved to yield sharp yet smooth edges, by any means which are well known in the art. Alternatively, such edges of barb 2 can be achieved by grinding the same, but grinding currently appears not to be a cost effective method as related to this application.

Dome 1 serves as a stress accumulating means wherein said dome 1 offers increasing resistance to applied pressure, directed inward, until said dome is deformed to an extent that it begins to undergo an inversion. At this point, resistance to the applied pressure decreases rapidly such that the central region of dome 1 containing the barb is accelerated inward and toward aperture 7 of pressure plate 3. With continued pressure dome 1 is inverted, directing barb 2 through aperture 7 and into the adjacent skin, thereby creating a puncture site.

An alternative embodiment is contemplated wherein said cover plate 21 and said pressure plate 3 are made from a single piece of material. Cover plate 21 and pressure plate 3 are folded against each other so as to share a common edge, the outer edges of each plate being secured to one another utilizing welds 4 or crimps 6 as discussed previously herein.

In its inverted state, dome 1 assumes an essentially cantilever configuration which accumulates a force opposing the inversion and aids in the resilient return the dome 1 to its convex configuration.

Figure 5:
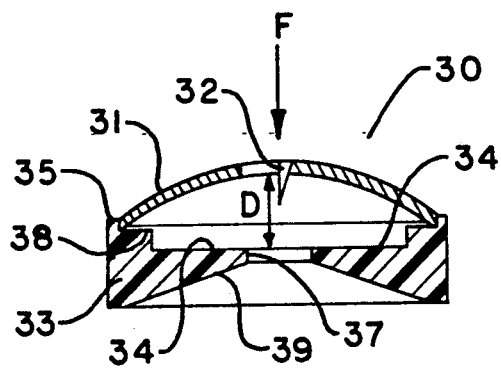
FIG. 5 is a cross-sectional view of an alternative embodiment of a skin perforator according to my invention illustrating a dome its uncollapsed position.
Figure 6:
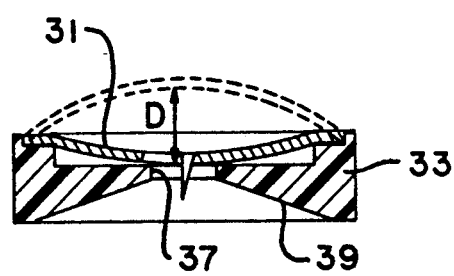
FIG. 6 is a cross-sectional view of the skin perforator shown in FIG. 5 and illustrating the dome in its collapsed position.

FIGS. 5 and 6 disclose an alternative embodiment 30 of the skin perforator. The pressure plate 33 is preferably made from a molded plastic material and is essentially annular in shape. A convex dome 31, similar to dome 1 of FIG. 1 and having a point penetrating barb 32, is seated on a step 38 and inside of an outer rim 35 in pressure plate 33. Pressure plate 33 contains an aperture 37 in its center which allows passage of barb 32 therethrough. Shelf 34 serves to stop the inversion of dome 31, thereby controlling the depth of barb 32 into the patient's skin.

In order to achieve a quick and relatively painless penetration of the skin, distance D between the peak of dome 31, in its undepressed state, and shelf 34 of pressure plate 33 is preferably at least about 0.10 inches. While this distance is not absolute, it has been calculated to account for a minimum stroke depth, deflection waste and differences in patient skin texture. According to the present embodiments, the minimum depth stroke is identified as that distance necessary for the dome to undergo its inversion and is estimated at 0.050 inches. The deflection waste refers to the movement of the dome 31 toward the puncture site upon the application of force but prior to the dome's inversion and is calculated at about 0.025 inches. Approximately 0.030 inches is necessary to account for differences in the thickness and texture of the skin at the puncture site. A distance D ranging from about 0.075 inches to about 1.025 inches insures penetration of the skin coupled with a positive return of the inverted dome to its convex configuration.

The present device 20 is designed to perforate the skin on the finger of the patient. The finger should be prepared so as to cleanse and remove as many contaminates from the perforation site as is possible using techniques which are well known in the art.

Figure 7:
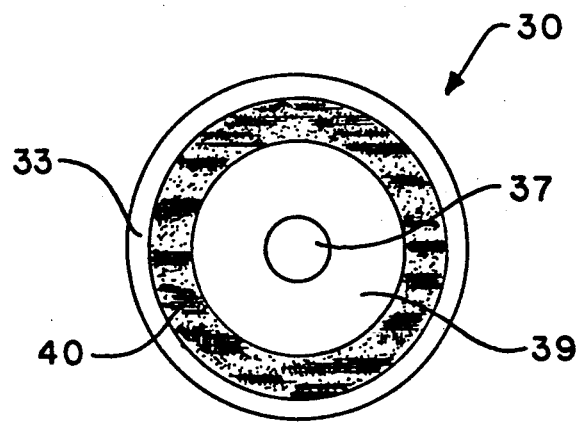
FIG. 7 is an bottom elevational view of an alternative embodiment of a skin perforator according to my present invention illustrating a self-contained means for cleaning and/or disinfecting the puncture site.

Optionally, any of the embodiments disclosed herein are contemplated as capable of incorporating a self-contained cleaning means disclosed in FIG. 7. Device 30 is shown as incorporating an absorbent pad, impregnated with a cleansing and/or disinfecting agent, affixed to the lower surface 39 of pressure plate 33, adjacent the patient's skin.

The absorbent pad 40 is intended to be made from any cotton, synthetic or other fiber commonly used in the art for such purpose and capable of retaining liquid therein. The cleansing or disinfecting agents can be selected from any such agents known in the art, including but certainly not limited to ethyl alcohol, isopropyl alcohol or benzalkonium chloride.

The lower surface 39 of pressure plate 33 is aseptically covered or sealed to keep the surface free from contaminates and to prevent evaporation of the cleansing agent. Immediately prior to use, a packaging seal is removed thus exposing the device and/or lower surface 39. The eventual puncture site can then be cleansed or disinfected by rubbing lower surface 39 of device 30 over the site. Often times, the puncture site is a fingertip, at which time the device is simply rubbed between the thumb and fingertip. In this manner, the eventual puncture site is cleansed and prepared to receive the point penetrating barb.

Figure 8:
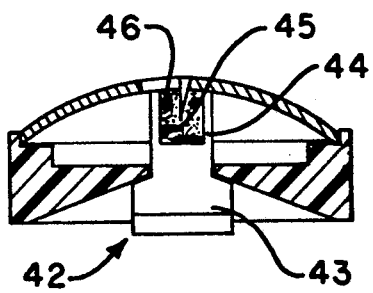
FIG. 8 is a cross-sectional view of skin perforator according to my present invention and illustrating a removable guard incorporated therein for maintaining the sterility of barb until use.

FIG. 8 reveals a means for preserving the sterility of barb 32 until just prior to the time of desired use. This packing means is disclosed as a tab 42 having a base portion 43 and a stem 44. The stem 44 is formed with a cavity 45 open at the end opposite base 43. Cavity 45 has a depth at least equal to the length of barb 32 in dome 31. Cavity 45 is capable of receiving a wax or other medium exhibiting properties of a solid at or above room temperature but liquefying in the presence of heat. Additionally, such medium must possess the ability to prevent or resist the growth of bacteria, fungi and other microbes, either inherently or by the addition of antimicrobials.

Following the sterilization of barb 32 after assembly, cavity 45 in stem 44 is filled with a medium 46 in a liquid or semi-solid state. Immediately thereafter, barb 32 is inserted into the medium contained in cavity 45. Thereupon cooling, a frangible connection between tab 42 and barb 32 is formed. Tab 42 is removed prior to use of the skin perforator by pliably moving tab 42 relative to device 30. Other means of frangibly connecting tab 42 about barb 32 as are known in the art to accomplish the same or similar purpose, are contemplated, such as ultrasonic welding and the like.

Turning again to FIGS. 1-3 but having applicability to all embodiments, the device 20 is operated by positioning said device 20 against the patient's finger to be punctured so that the intended puncture site of the finger comes within a area defined by the outer circumference of aperture 7 in pressure plate 3. Pressure is then applied to the dome by the patient or person assisting the same. The initial applied pressure causes pressure plate 3 to be pressed against the skin of the patient further isolating the intended puncture site. As additional pressure is applied to dome 1 the stress accumulation in the dome will result in the sudden inward collapsing of dome 1, directing barb 2 through aperture 7, thereby causing a piercing of the patient's skin. This inward movement of barb 2 is stopped as the inner surface of dome 1 strikes shelf 23 of pressure plate 3 to provide a predictable puncture depth.

As the applied pressure on dome 1 and pressure plate 3 is removed or reduced, the collapsed dome will resiliently return to its original shape and accordingly withdraw barb 2 from the patient's finger. The maintenance of a small amount of pressure against pressure plate 3, but pressure insufficient to cause collapse of dome 1, will create a tension to the area around the puncture site, resulting in an enhanced and continuous blood flow from the puncture site. This applied tension has a twofold effect with respect to enhanced blood flow. First, this tension maintains the skin in a stretched posture which holds edges of the puncture site apart. Second, the pressure applied to the region surrounding the puncture site forces blood out of this tissue and into adjacent tissue which may be outside or inside of this ring of applied pressure. The blood directed inward seeks relief from this pressure and as a result exits through the puncture site. Flow enhancement of the blood from the puncture site is also increased by the creation of a partial vacuum or pressure differential within the confined area defined by dome 1, pressure plate 3 and the patient's finger. This area as defined while the dome is in the collapsed position, has a comparatively reduced volume compared to the same area with dome 1 in its original position. While in the depressed position, the person administrating the applied force may simply cover or obstruct aperture 10 formed from the stamping of barb 2, as the pressure is withdrawn. This sudden increase in volume in the area enclosed by the pressure plate 3 and dome 1 creates a vacuum at the aperture 7. The vacuum causing free flow of blood from the puncture site.

After the barb has been withdrawn from the finger, the disposable skin perforator can be removed and a blood sample collected as in prior art devices by squeezing the finger, if necessary.

Figure 3:
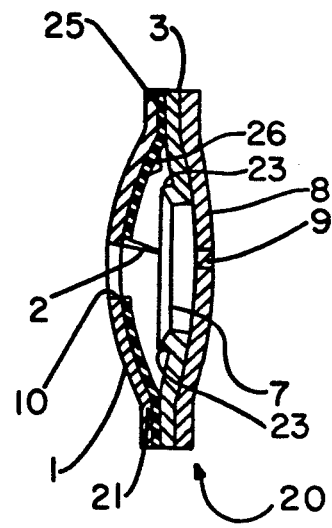
FIG. 3 is a cross-sectional view similar to FIG. 2 further illustrating a sealing means and a step formed on the surface of pressure plate.

To further effect a vacuum in the confined area of perforator device 20, a seal or gasket 25 can be placed between the cover plate 21 and the pressure plate 3 as is shown in FIG. 3. This seal or gasket 25 can be made from a variety of flexible plastic or rubber materials as is well known in the art and serves to prevent air passage into and out of the confined area of perforator device 20 through the contact between the peripheral edges of cover plate 21 and peripheral plate 3. A preferred manner of creating a seal or gasket 25 is to apply a laminate to the inner surface of either the cover plate 21 or the pressure plate 3. Such laminate becomes sandwiched between cover plate 21 and pressure plate 3 during the application of welds 4 or crimps 6.

Figure 4:
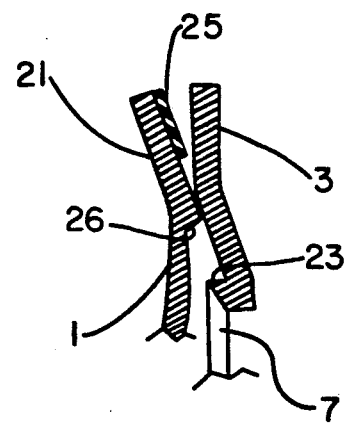
FIG. 4 is a cutaway cross-sectional view illustrating the dome in a depressed position and a step causing the formation of a means for air exchange.

Still another embodiment which is contemplated to create a vacuum for improving flow enhancement is a formation of one or more steps 26 in pressure plate 3. These steps 26 are essentially projections of varying width formed on the inner surface of pressure plate 3 or cover plate 21 along its periphery and located between the crimper 6 or welds 4. Steps 26 are of sufficient size so as to extend into the area defined by and below the dome 1. Steps 26 do not interfere with the depression of the dome but contact the opposing surface after substantial depression of the dome. As dome 1 is depressed to effectuate a puncture, steps 26 cause sufficient deflection along the periphery of cover plate 21 to form a temporary break in the seal between cover plate 21 and pressure plate 3 as shown in FIG. 4. This break allows for the exit of air trapped within the confined area of the perforator device 20. Following puncture of the finger by barb 2, and the gradual withdrawal of the applied pressure from dome 1, the seal 25 is reformed thereby creating the vacuum to enhance blood flow from the puncture site.

Figure 2:
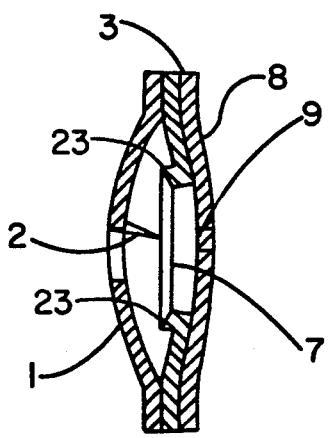
FIG. 2 is a cross-sectional view taken on line 2—2 of FIG. 1.

The present invention, in a further preferred embodiment, comprises an absorbent test strip 8 and is best illustrated in the cross-sectional views of FIGS. 2 and 3. Test strip 8 is disclosed as generally a pad or sheet of material capable of absorbing blood or exudate from the puncture site created by barb 2. The test strip 8 is contemplated as being treated or coated with various reagents which react with the blood or exudate to cause color or chemical changes which then can be quantitatively or qualitatively compared to a known standard. Most home use test strips utilize color change techniques and yield fairly quick results which can be interpreted by comparing the test strip to a color coded chart provided with the device. The most common test strip contemplated is that used for the determination of the patient's blood sugar level. The technology of such test strips is well known in the art.

Test strip 8 is disclosed as being laminated to the outer surface of pressure plate 3. Lamination may be done using known adhesives or by means of crimps 6. Test strip 8 may be of varying shapes or sizes but preferably has a length slightly greater than the diameter of aperture 7. Although, not required, test strip 8 contains a aperture dimensioned and positioned to allow passage of barb 2 therethrough. In this embodiment the device is used similar to that as described previously herein. However, test strip 8 is positioned immediately adjacent to the patient's finger with the aperture 9 in the test strip 8 identifying the intended test site.

Following the puncture of the patient's finger by barb 2, the disposable skin perforator 20 remains in contact with the finger to allow the blood or exudate from the puncture site to be absorbed onto test strip 8. Maintenance of a pressure pressing pressure plate 3 against the finger, but which is insufficient to cause collapse of dome 1, will enhance blood flow as previously described and allow for saturation of test strip 8 with the blood or exudate from the puncture site.

This device, incorporating test strip 8 places the test medium immediately adjacent to the puncture site and allows blood collection and testing to begin immediately upon puncture. Furthermore, test strips 8 representing various thickness may be used. Such strips 8 can extend into the recession found in the bottom surface of pressure plate 3 by shelf 23. In a less preferred, but contemplated embodiment, test strip 8 would omit the formation of aperture 9 therein. Barb 2 is of sufficient length and sharpness to cut test strip 8 simultaneously with the skin of the fingertip. However, it is thought that such a practice may permit the introduction of fibrous material from test strip 8 into the puncture site formed by barb 2.

The skin perforators of the present invention are intended as disposable or single use devices, unless the devices are resterilized after each use by means known in the art. In this way, the risk of patient contamination resulting from the use of unsterile or tainted devices is minimized. In furtherance of this objective, the skin perforator shown in FIGS. 8-17 incorporate a shutter means for preventing repeated use of the device.

Generally, the device is fully functional upon its removal from the aseptic packaging. The device is used to perforate the skin of a patent for the purposes of obtaining a blood sample by placing the pressure plate in contact with the skin and applying force to the convex dome as previously described. In these embodiments, the force applied to cause inversion of the dome resulting in the puncture of dome by barb 32 is also utilized to fracture or otherwise disable a stop member functioning to hold a shutter device in its tensioned position. Upon retraction of the dome, the shutter means will advance to its untensioned position between barb 32 and aperture 37. In this way, subsequent attempts to utilize device 30 as a skin perforator will force barb 32 against the shutter, preventing puncture of the patient's skin. Once the shutter means has advanced to its untensioned position between barb 32 and aperture 37, the device is disabled and to be discarded.

Figure 9:
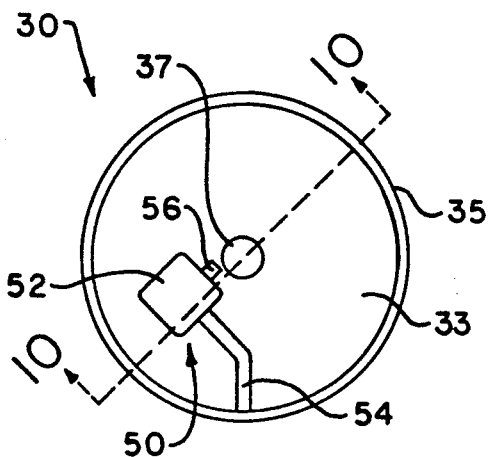
FIG. 9 is a top elevational view of a skin perforator according to my present invention illustrating a shutter means for preventing multiple use, in its tensioned state.
Figure 11:
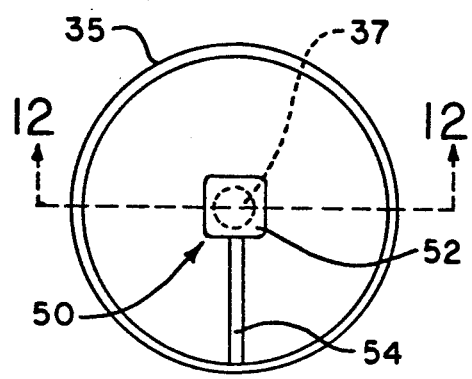
FIG. 11 is a top elevational view of the skin perforator shown in FIGS. 9 and 10, illustrating the shutter means in its untensioned state.
Figure 10:
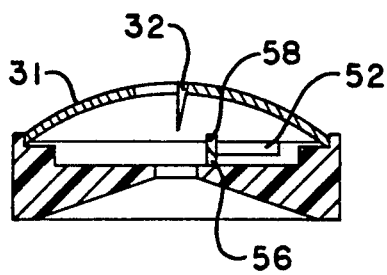
FIG. 10 is a cross-sectional view of the skin perforator in FIG. 9, taken across line 10—10.

Specifically, FIGS. 9-12 illustrate one embodiment of a shutter means for preventing repeated use of a skin perforator. FIGS. 9 and 11 disclose the shutter means generally 50, having a shield portion 52 and a stem portion 54. The stem 54 is contemplated as an essentially rigid material having a substantially long term memory so as to return to its original untensioned position even after extended periods of time in a tensioned state. Such suitable materials include but are not limited to various types of plastics or aluminum. The proximal end of stem 54 is shown as attached to an inner wall of the pressure plate 33 although it is to be recognized that alternative sites of attachment are possible.

A shield member 52 is secured to the distal end of stem 54. The shield member 52 is intended as having a total area approximately equal or greater than to aperture 37.

Stop member 56 is located between aperture 37 and shutter means 50 and serves to maintain the shutter means 50 in a tensioned position until completion of the device's initial use. Step member 56 is intended to be constructed with sufficient strength to enable it to hold shutter means 50 in a tensioned position but capable of fracturing, deforming, pivoting or otherwise yielding to the force of the skin perforator's activating mechanism, in this case the dome, in order to release the shutter means thereby preventing further use of this particular device.

Figure 12:
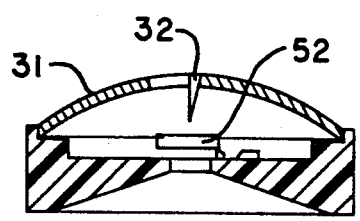
FIG. 12 is a cross-sectional view of the skin perforator shown in FIG. 11, taken along line 12—12.
Figure 13:
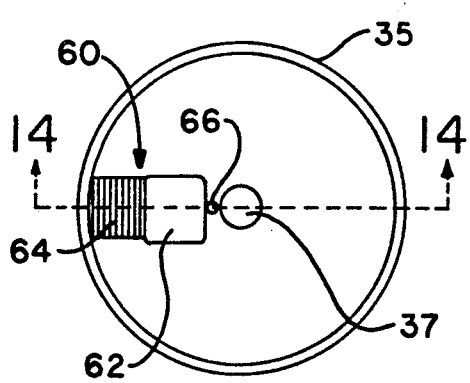
FIG. 13 is a top elevational view of a skin perforator according to my present invention illustrating an alternative shutter means for preventing multiple use in its tensioned state.
Figure 15:
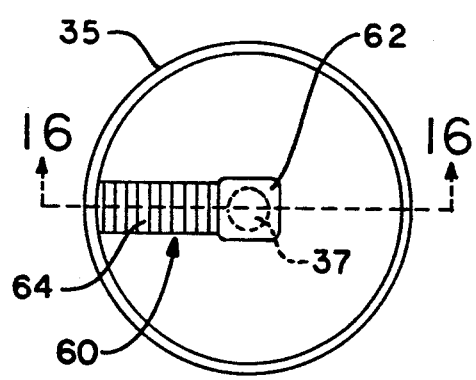
FIG. 15 is a top elevational view of the skin perforator shown in FIGS. 13 and 14 and illustrating the shutter means in its untensioned state.

Stop member 56 is contemplated as being made from material similar to pressure plate 33 and formed integrally therewith. A frangible connection or weakened portion 58 is formed therein but possessing sufficient strength to withstand the pressure of a tensioned shutter means 50. Upon compression of dome 31 from applied force, the frangible connection 58 is broken as the barb penetrates the skin. Upon retraction of dome 31 to its original position, shutter means 50 advances to its untensioned position as illustrated in FIGS. 11 and 12 with shield 52 covering aperture 37. In this way, subsequent attempts to utilize device 30 will result in the barb's contact with shield 52 thereby preventing additional punctures of the skin using the same device.

FIGS. 13-16 illustrate an alternative shutter means 60 utilizing the same general principles previously discussed. Shutter stem 64 is secured to an inner wall of pressure plate 33 by any means known in the art and is formed from any corrugated material capable of returning to an elongated position following compression. Stop member 66 is disclosed as a raised projection originating from surface 34 and formed integrally therefrom. Stop member 66 is compressed into a void or weakened region of pressure plate 33 by the force of the dome 31 as it directs the barb 32 into the skin.

Figure 14:
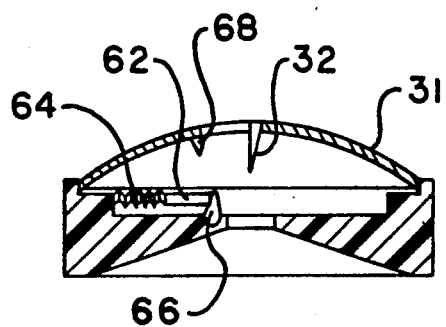
FIG. 14 is a cross-sectional view of the skin perforator shown in FIG. 13 taken along line 14—14.
Figure 16:
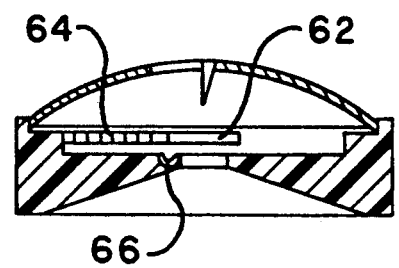
FIG. 16 is a cross-sectional view of the skin perforator as shown in FIG. 15 taken along line 16—16.

The shuttle means as illustrated in the embodiments previously disclosed herein need only possess sufficient tension to enable it to position itself between the barb and the aperture. Preferably the tension applied to the shutter means is not so great as to cause contact with the barb, while in the patients skin. Alternatively, a retaining means 68 as shown in FIG. 14 may be formed in or on dome 31 to delay the advance of the shutter means to its untensioned position until after the barb is withdrawn from the puncture site.

Figure 17:
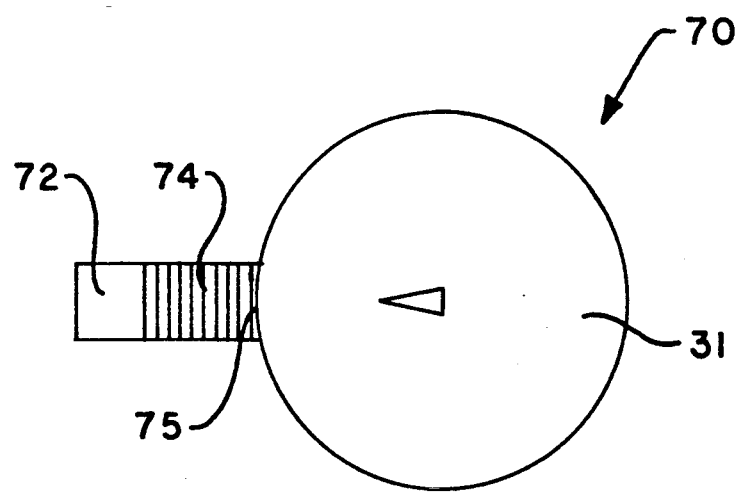
FIG. 17 is a top elevational view of a convex dome for a skin perforator according to my present invention having a integrally formed shutter means.

FIG. 17 shows a dome 31 and shutter means 70 formed as a single unit from resilient metal or plastic materials. One such embodiment is contemplated as being formed from the stamping of a resilient metal material as described previously with respect to dome 1.

Shutter means 70 is folded towards the interior of dome 31 along line 75. During assembly, stem 74 is compressed in order that shutter 70 is retained in a tensioned state until actuated by a stop member. The shutter means detailed in the drawings and specification of this application are illustrative and not to be construed as limited to the specific embodiments set forth herein. It is contemplated that the self-contained cleansing means and the shutter means have application well beyond the scope of the specific embodiments of skin perforators disclosed in this application.

Hence the foregoing embodiments are designed to be simple in construction, economical to manufacture and capable of being packaged under sterile conditions. The various embodiments of the present invention are contemplated as being either disposable or reusable following sterilization using known techniques. While in accordance with the patent statutes the best mode and preferred embodiment of the invention have been described, it is to be understood that the invention is not limited thereto, but is rather to be measured by the scope and the spirit of the appended claims.

What is claimed is:

1. A skin perforator for obtaining a sample of blood by puncturing the skin comprising:
    a) a pressure plate containing an aperture formed therein wherein said pressure plate is placed adjacent to and surrounding the area of skin to be punctured;
    b) a cover plate having a resilient convex panel formed therein, said cover plate being attached to said pressure plate and said convex panel having a point penetrating barb formed integrally therefrom and directed inward toward said aperture in said pressure plate, said integrally formed barb resulting in an aperture formed in said convex panel, wherein a first and second pressure are applied the convex panel and directed toward said pressure plate, said second pressure being greater than said first pressure so that said convex panel has a resistance to said first pressure and as said first pressure is increased toward said second pressure, said pressure overcomes the resistance of said convex panel and said convex panel collapses rapidly to cause said barb to suddenly and rapidly penetrate the skin causing a puncture, said convex panel resiliently returning to its original convex shape upon removal of said pressure thereby withdrawing the barb from the skin, and (c) a means for limiting said barb to a single penetration of the skin wherein said limiting means automatically occludes the aperture of said pressure plate following the initial penetration.

2. The skin perforator as recited in claim 1 wherein said limiting means is activated by the inversion of said convex panel.

3. The skin perforator as recited in claim 1 wherein said limiting means comprises a shutter having a shield portion and a stem portion, said shutter portion being dimensioned approximately equal to or greater than the aperture in said pressure plate, said stem portion capable of accepting applied tension and having a memory so as to advance predictably upon removal of said tension.

4. The disposable skin perforator as recited in claim 1 wherein said limiting means further comprises a stop member for retaining said limiting means in a tensioned position.

5. The skin perforator as recited in claim 4 wherein said stop member has sufficient strength to retain said limiting means in a tensioned position but yields to a force applied during the inversion of said convex panel to release the tension applied to said limiting means.

6. The skin perforator as recited in claim 1 further comprising an absorbent test strip attached to said pressure plate to absorb blood or exudate flowing from a puncture site formed by the penetration of said barb.

7. The skin perforator as recited in claim 6 wherein said test strip is treated with at least one reagent for medical analysis.

8. The skin perforator as recited in claim 1 and further comprising an applying means for applying a preparatory agent to the skin.

9. The skin perforator as recited in claim 8 wherein said applying means comprises a pad of absorbent material impregnated with a skin preparatory agent.

10. The skin perforator as recited in claim 9 wherein said absorbent pad is an essentially annular ring circumscribing the aperture in said pressure plate.

11. The skin perforator as recited in claim 8 wherein said preparatory agent comprises one or more from the group consisting of ethyl alcohol, isopropyl alcohol, benzalkonium chloride, iodine, and topical antimicrobials.

12. A skin perforator for puncturing the skin, said perforator of the type comprising a housing having a contact surface for placement adjacent to the skin to be punctured, an aperture in said contact surface, a puncturing member operatively mounted within said housing for movement towards and through said aperture, wherein the improvement comprises:

a limiting means for automatically occluding the aperture of said skin perforator following initial puncture of the skin.

13. The skin perforator as recited in claim 12 and further comprising an applying means for applying a preparatory agent to the skin.

14. The skin perforator as recited in claim 13 wherein said applying means comprises a pad of absorbent material impregnated with a skin preparatory agent.

15. The skin perforator as recited in claim 14 wherein said absorbent pad is an essentially annular ring circumscribing the aperture in said contact surface.

16. The skin perforator as recited in claim 13 wherein said preparatory agent comprises one or more from the group consisting of ethyl alcohol, isopropyl alcohol, benzalkonium chloride, iodine, and topical antimicrobials.

17. The skin perforator as recited in claim 12 wherein said limiting means comprises a shutter having a shield portion and a stem portion, said shutter portion being dimensioned approximately equal to or greater than the aperture in said pressure plate, said stem portion capable of accepting applied tension and having a memory so as to advance predictably upon removal of said tension.

18. The disposable skin perforator as recited in claim 12 wherein said limiting means further comprises a stop member for retaining said limiting means in a tensioned position.

19. The skin perforator as recited in claim 18 wherein said stop member has sufficient strength to retain said limiting means in a tensioned position but yields to a force applied during the initial puncture of the skin to release the tension applied to said limiting means.

20. The skin perforator as recited in claim 12 wherein said skin perforator further comprises a directing means for receiving an external force and applying said force to said puncturing member upon activation, for directing said puncturing member into the skin.

21. The skin perforator as recited in claim 20 wherein said directing means is a resilient convex panel mounted on the housing and wherein an external force applied to said convex panel overcomes the resistance of said panel, causing said panel to undergo at least a partial inversion which results in the rapid penetration of the skin, said convex panel having memory so as to resiliently return to its original convex shape upon removal of said force thereby withdrawing said barb from the skin.

22. The skin perforator as recited in claim 21 wherein said limiting means is activated by the inversion of said convex panel.

* * * * *